United States Patent
Curley et al.

[11] Patent Number: 5,846,205
[45] Date of Patent: Dec. 8, 1998

[54] CATHETER-MOUNTED, PHASED-ARRAY ULTRASOUND TRANSDUCER WITH IMPROVED IMAGING

[75] Inventors: Michael G. Curley, Cambridge, Mass.; Diana M. Tasker, Mountain View, Calif.; Cynthia C. Becker, Santa Clara, Calif.; Randall L. Schlesinger, San Mateo, Calif.; John W. Eaton, Palo Alto, Calif.

[73] Assignee: Acuson Corporation, Mountain View, Calif.

[21] Appl. No.: 791,598

[22] Filed: Jan. 31, 1997

[51] Int. Cl.[6] .................................................... A61B 8/12
[52] U.S. Cl. ........................................... 600/472; 600/463
[58] Field of Search ........................... 128/660.03, 660.1, 128/662.05, 662.06, 916

[56] References Cited

U.S. PATENT DOCUMENTS

| | | |
|---|---|---|
| 3,938,502 | 2/1976 | Bom . |
| 4,605,009 | 8/1986 | Pourcelot et al. .................. 128/662.06 |
| 4,794,931 | 1/1989 | Yock . |
| 4,841,977 | 6/1989 | Griffith et al. ...................... 128/660.03 |
| 4,917,097 | 4/1990 | Proudian, et al. . |
| 4,947,852 | 8/1990 | Nassi et al. ........................... 128/662.06 |
| 5,291,893 | 3/1994 | Slayton .............................. 128/662.06 |
| 5,297,553 | 3/1994 | Sliwa, Jr. et al. . |
| 5,325,860 | 7/1994 | Seward et al. . |
| 5,345,940 | 9/1994 | Seward et al. . |
| 5,368,037 | 11/1994 | Eberle et al. . |
| 5,375,602 | 12/1994 | Lancee et al. ...................... 128/662.06 |
| 5,398,689 | 3/1995 | Connor et al. . |
| 5,400,785 | 3/1995 | Crowley ............................. 128/662.06 |
| 5,417,219 | 5/1995 | Takamizawa et al. . |
| 5,476,107 | 12/1995 | Oakley et al. ...................... 128/898 X |
| 5,562,096 | 10/1996 | Hossack et al. . |
| 5,699,805 | 12/1997 | Seward et al. . |
| 5,704,361 | 1/1998 | Seward et al. . |
| 5,713,363 | 2/1998 | Seward et al. . |

OTHER PUBLICATIONS

Seward, J.B., D.L. Packer, R.C. Chan, M.G. Curley, A.J. Tajik (Jul. 1996), "Ultrasound Cardioscopy: Embarking on a New Journey," Mayo Clinic Proceedings, 71(7):629–635.

Wells, *Biomedical Ultrasonics*, Academic Press 1977, pp. 38–42.

*Primary Examiner*—Francis J. Jaworski
*Attorney, Agent, or Firm*—Brinks Hofer Gilson & Lione

[57] ABSTRACT

A phased-array ultrasonic transducer assembly includes a catheter. An end portion is mounted to the catheter around a transducer array, and the end portion defines an acoustic window which is essentially non-focusing to ultrasonic energy passing therethrough. Because the acoustic window is non-focusing, a relatively small radius of curvature can be used on the radially outer surface of this window.

23 Claims, 4 Drawing Sheets

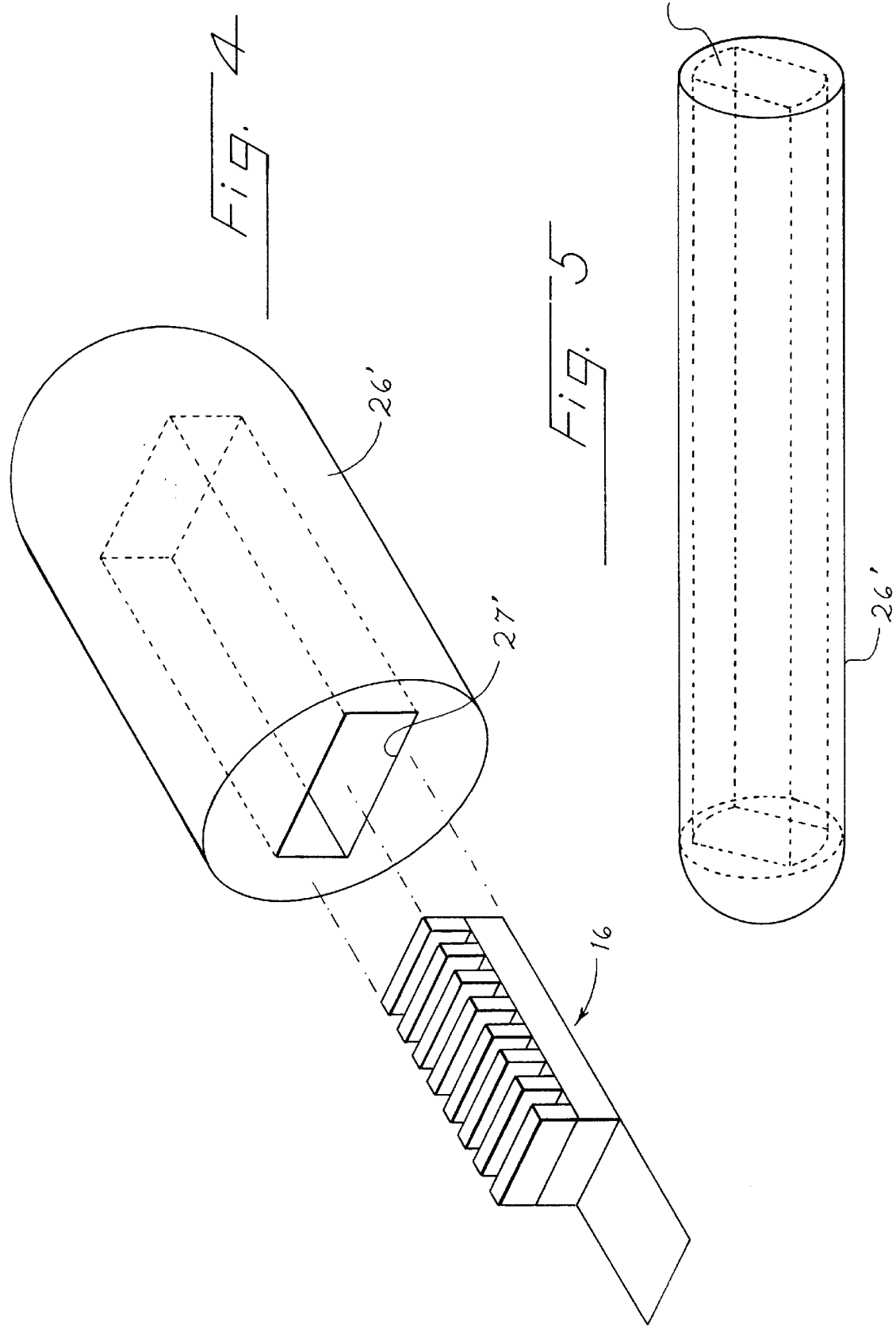

CATHETER-MOUNTED, PHASED-ARRAY ULTRASOUND TRANSDUCER WITH IMPROVED IMAGING

BACKGROUND OF THE INVENTION

This invention relates to catheter-mounted ultrasonic transducers of the phased-array type, and in particular to improvements in such catheters that improve the focus of the transducer in the elevation direction.

Catheter-mounted ultrasonic transducers have in the past taken several forms, including (1) single-element transducer crystals that are pointed radially outward and rotated about the axis of the catheter, (2) radial array transducers, and (3) linear array transducers. Bom U.S. Pat. No. 3,938,502 discloses one catheter-mounted ultrasonic array which utilizes a radial array arranged circumferentially around the axis of the catheter. Proudian U.S. Pat. No. 4,917,097 describes a similar radial array (and alludes to other geometries) that require multiplexing of the ultrasound signals near the elements of the array. Seward et al. (Seward, J. B., D. L. Packer, R. C. Chan, M. G. Curley, A. J. Tajik (1996), "Ultrasound Cardioscopy: Embarking on a New Journey," *Mayo Clinic Proceedings*, 71(7)) have described a phased array transducer for insertion into the heart. Such an array has the advantage of increased power: as the transducer array is made longer, the number of elements can be increased, thereby increasing the total radiation area.

Conventional phased-array, linear ultrasonic transducers are typically constructed using a piezoelectric material such as PZT. The piezoelectric material is formed into individual elements, arranged side by side with the lengths of individual elements parallel to one another. PZT is typically built on a backing material that reflects most of the ultrasound energy generated by the PZT, and also tends to absorb energy that is coupled into it. The active surface of the PZT is covered with a second material, called the matching layer, that couples ultrasonic energy from the PZT into the tissue that the transducer is in contact with. The backing material and the matching layer are typically made of composite material such as epoxy loaded with a heavier material such as alumina. By adjusting the phase of waveforms applied to the PZT elements, ultrasonic energy can be focused and steered within a plane oriented parallel to the array and the catheter axis. The techniques for designing transducers and steering them are discussed in texts such as Kino (*Acoustic Waves*, Prentice Hall, Englewood Cliffs, 1987) and Wells (*Biomedical Ultrasonics*, Academic Press, London, 1977).

FIG. 7 shows a prior-art, linear, phased-array transducer, and identifies the X, Y and Z coordinates for this transducer. In FIG. 7, the PZT material is identified by the reference symbol P, the backing material by the reference symbol B, and the matching layer by the reference symbol M. By properly controlling phase of the transducer signals applied to the individual piezoelectric elements P, the location and size of the focal spot in the XZ plane can be controlled. The size of the focal spot in the Y dimension is typically determined by a lens applied to the transducer. Such a lens focuses ultrasonic energy in the Y direction by taking advantage of the difference in the speed of sound in the lens material and in tissue in contact with the lens. If a lens has a speed of sound that is slower than that of adjacent tissue and is convex in shape, ultrasonic energy is caused to converge in the ZY plane. The ultrasonic energy focuses in a spot that is spaced from the piezoelectric elements P by a distance controlled by the radius of curvature of the lens and also by the difference in speed of sound between the lens and the adjacent tissue. As the speed of sound of the lens is made increasingly slower than that of adjacent tissue or as the radius of curvature of the lens is made progressively smaller, the focal spot approaches more closely to the transducer. When the focal spot is positioned close to the transducer, the width of the ultrasonic field rapidly diverges as the wave propagates past the focal spot. Of course, if the speed of sound in the lens is faster than in the adjacent tissue, the lens material would be formed in a concave shape to obtain the desired focusing.

It is desirable to maintain the width of the ultrasound field as thin as possible in the Y dimension. This keeps the intensity of the ultrasound energy as high as possible, which increases the strength of the reflected signal when the ultrasound is reflected by structures in the tissue. It is also desirable to keep the thickness of the field in the Y dimension as uniform as possible as the ultrasound propagates in the Z direction. This is because reflections of ultrasound energy at any particular depth that are detected at the transducer represent the integrated reflected energy within the ultrasound wave at that depth. If the ultrasound field is too wide, an object causing a reflection may be indistinguishable from the surrounding tissue. If the thickness of the ultrasound field varies from thin to thick as it propagates in Z, then an object that might be detected where the field is thin might not be detected where the field is wide, which is confusing and counterintuitive to the physician. Thus, it is desirable to maintain a thin, but uniform, ultrasound field width in the Y dimension as the wave propagates in the Z dimension.

Seward, et al. (Seward, J. B., D. L. Packer, R. C. Chan, M. G. Curley, A. J. Tajik (1996), "Ultrasound Cardioscopy: Embarking on a New Journey," *Mayo Clinic Proceedings*, 71(7)) have described a phased array ultrasound transducer for insertion into the heart. This transducer utilizes a linear phased array of the type shown in FIG. 7, and it offers many improvements over catheter-based radial imaging transducers of the past. These advantages are detailed in the Seward paper, but can be briefly listed as follows: the image plane is advantageous when imaging therapeutic interventions in the heart; the overall aperture of the transducer is large, improving the ultrasound energy and the penetration depth of the tissue; and the transducer is compatible with modern ultrasonic scanning systems.

The Seward transducer is made of conventional materials, including an epoxy-based backing block and a silicone-based lens. The transducer is constructed of 128 elements operating at 5 or 7 MHz. The total array extends for 14 mm in the X direction and 3.3 mm in the Y direction. The backing block is 5 mm in depth or more. As such, the overall diameter of this catheter is 8 mm. If the lens were formed into a cylinder with an 8 mm diameter, it would cause the ultrasound focus to be too close to the transducer, and the ultrasound field would then begin to diverge quickly, causing a loss of image quality and a loss of sensitivity and penetration depth. For this reason, the lens of the Seward transducer is flattened in the region of the transducer, making the forming of the final catheter more difficult.

A need presently exists for a catheter mounted, linear, phased-array transducer that is smaller in diameter and that can be more easily manufactured.

SUMMARY OF THE INVENTION

According to this invention, a phased array ultrasonic transducer assembly is provided comprising a catheter having a distal end and defining a longitudinal axis. An array of transducer elements is carried by the distal end of the catheter, and this array defines an azimuthal axis extending substantially parallel to the longitudinal axis. The catheter comprises an end portion positioned adjacent to and radially outwardly from the array, and this end portion conducts ultrasound waves to and from an active service of the array with a speed greater than about 1,250 meters per second. The end portion is characterized by a maximum cross-sectional dimension that is less than about 8 mm.

BRIEF DESCRIPTION OF THE DRAWINGS

FIG. 4 is an exploded prospective view showing an alternate construction for the catheter of FIG. 1.

FIG. 5 is a perspective view of the end portion of FIG. 4.

DETAILED DESCRIPTION OF THE PRESENTLY PREFERRED EMBODIMENTS

Figure 1:
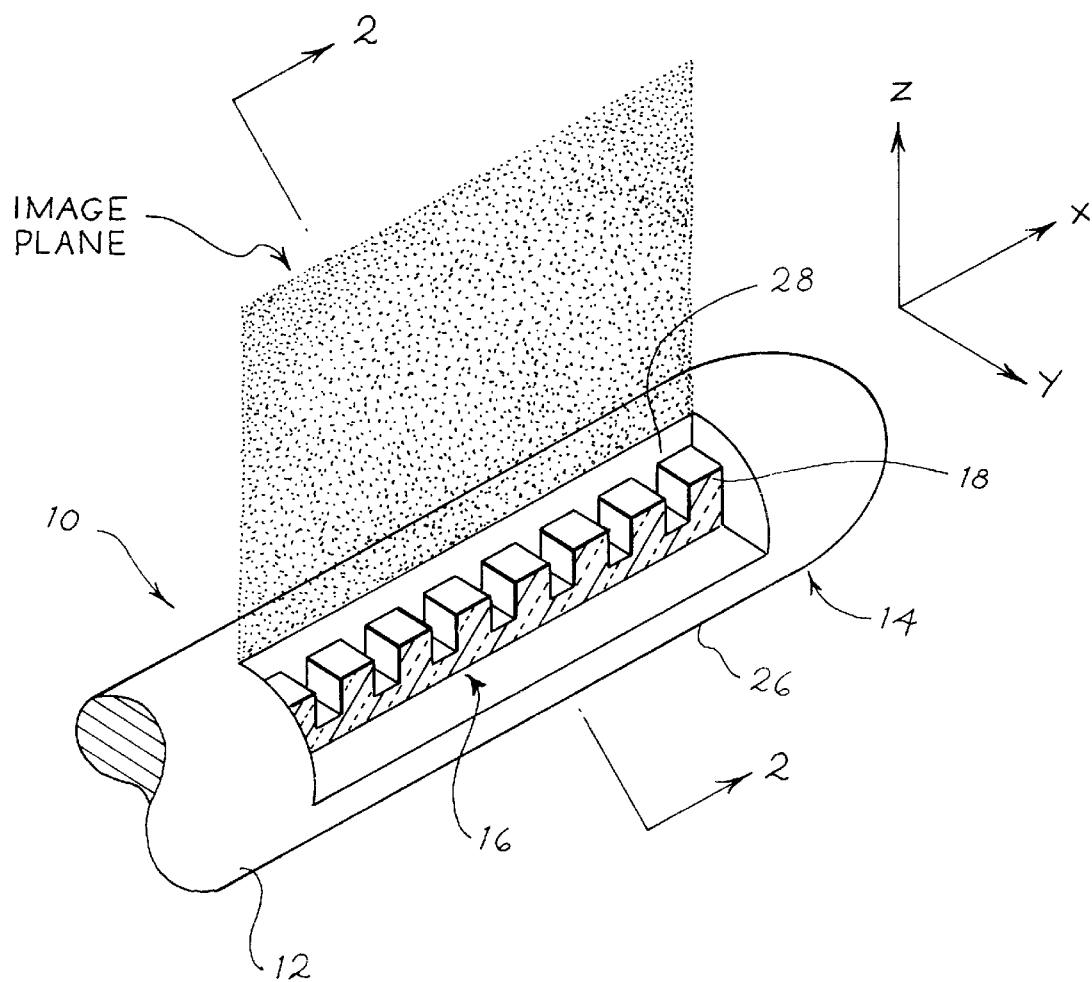
FIG. 1 is a perspective view in partial cutaway of a portion of a catheter-mounted transducer that incorporates a presently preferred embodiment of this invention.

Turning now to the drawings, FIG. 1 shows a perspective view of a transducer assembly 10 that incorporates a presently preferred embodiment of this invention. The transducer assembly 10 includes a catheter 12 which defines a distal end 14. In this embodiment the proximal end (not shown) is spaced from the distal end by about 110 centimeters, and the catheter 12 is circular in cross section and defines a maximum cross-sectional dimension of about 3.3 mm.

The distal end 14 of the catheter 12 carries a linear array 16 of transducer elements 18. The transducer elements 18 define an azimuthal axis which is denominated the X axis in FIG. 1, and is parallel to the longitudinal axis of the catheter 12.

Figure 2:
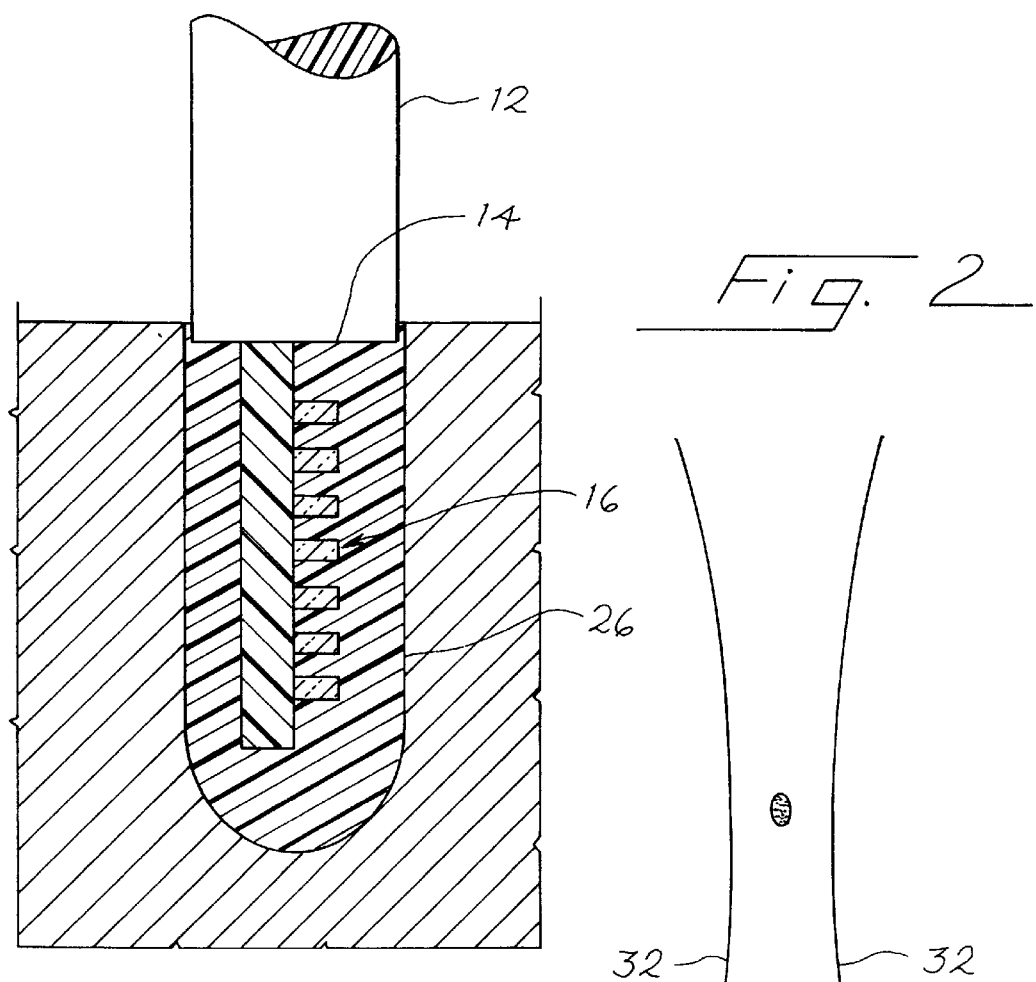
FIG. 2 is a cross-sectional view taken along line 2—2 of FIG. 1.

As shown in FIG. 2, the transducer array 16 includes a matching layer 20 adjacent the active surface of the transducer elements 18, and a backing layer 22 on the reverse side of the transducer elements 18. Flexible circuits are disposed in a lumen defined by the catheter 12 to carry transmit signals and receive signals between the individual transducer elements 18 and an ultrasonic diagnostic imaging system (not shown).

As shown in FIGS. 1 and 2, the catheter 12 includes an end portion 26 that is secured to the tube of the catheter 12 and surrounds the transducer array 16. The part of the end portion 26 that overlies the active surface of the transducer elements 18 forms an acoustic window 28. Typically, the end portion 26 and the acoustic window 28 may be formed of the same material, though this is not required. In this embodiment the end portion 26 is circular in cross section, and the radially outer surface 30 of the acoustic window 28 defines a radius of curvature which is substantially equal to one-half of the maximum cross-sectional dimension of the end portion 26. Since the end portion 26 is circular in cross section in this embodiment, the radius of curvature of the surface 30 is equal to the radius of curvature of the remaining parts of the end portion 26. This arrangement simplifies fabrication of the transducer assembly 10, because it eliminates both the need for a complex shape for the window, and the need for accurate registration between the transducer and the window.

Preferably the maximum cross-sectional dimension of the end portion 26 and the catheter 12 is less than 8 mm. This dimension is more preferably less than 3.3 mm, and most preferably less than 2 mm.

According to this invention, the acoustic window 28 is formed of a material that propagates ultrasonic waves at a speed comparable to or greater than the speed at which such ultrasonic waves propagate in adjacent tissue such as blood. As is known in the art, the propagation speed of ultrasound energy in blood is about 1570 meters per second, and the acoustic window 28 is preferably formed of a material having a comparable speed of sound for ultrasonic energy. The speed of sound in the window 28 is preferably greater than about 1250 m/sec. (1570 m/sec-20%), more preferably greater than about 1410 m/sec (1570 m/sec-10%), and most preferably greater than or equal to about 1570 m/sec. As used herein, the term "acoustic window" is intended to encompass both non-focusing and de-focusing elements between the active surface of the array and the tissue being scanned.

When the acoustic window 28 provides a speed of sound comparable to that of adjacent tissue, the radius of curvature of the radially outer surface 30 will not affect the focusing characteristics of the transducer array 16. In contrast, if conventional materials were used for the acoustic window 28 and the radius of curvature of the radially outer surface 30 were maintained at 1.5 millimeters (3 mm diameter for the end portion 26), the result would be an ultrasonic focus located too close to the transducer array 16. Such a close focus would cause the ultrasonic field to diverge rapidly at depths greater than the focal region, causing poor image quality and a loss of imaging depth.

However, it may be desirable to increase the thickness in the Y dimension if the natural thickness when the field is unfocussed is too thin. If the field is too thin, then objects would appear, then disappear from the image if the catheter, hence the ultrasound field, were rotated slightly. If the speed of sound in the material surrounding the transducer were greater than in the surrounding blood, and this material were convex, then the ultrasound field would diverge upon exiting the catheter. This would increase the thickness of the field in the Y dimension, which would have desirable properties for keeping objects in the image field with slight rotation of the transducer.

The design of the ultrasound imaging field may be different for different applications. When the image field needs to be wide, then a material with a speed of sound faster than that of blood can be used. When it is desirable to keep the image width narrow, and with minimal variation in the thickness of the image field, then a material with a speed of sound close to that of blood can be used.

In FIG. 2, lines 32 schematically show the ultrasonic field boundaries for the situation where the acoustic window 28 is formed of a material having a speed of sound close to that of tissue. If this material also has an acoustic impedance close to that of tissue, the ultrasound field generated by the transducer array 16 propagates as if it is simply contacting the tissue, and there is no significant reflection of the ultrasonic field as it exits the acoustic window 28. Similarly, there is no significant reflection of ultrasonic energy at this interface because of the substantially identical acoustic impedance on both sides of the surface 30.

Preferably, the length of each transducer element 18 in the Y direction is larger than a wavelength of ultrasonic energy, and the material of the acoustic window 28 is selected as described above. In this case the transducer array 16 will exhibit a gentle, natural focus. The distance in the Z dimension from the transducer array 16 to the location at which the thickness of the ultrasonic field in the Y dimension is smallest is approximately equal to $$FocalDepth = l^2 f/2c,$$

where c is the speed of sound in tissue (1570 m/sec), l is the elevational length of the transducer elements 18, and f is the ultrasound frequency. When the transducer 16 measures 2.5 mm in the Y dimension and operates at 7 MHz in a 3.3 mm diameter catheter having an acoustic window as described above, the point of best focus is approximately 14 mm away from the transducer array 16. Beyond this depth the ultrasound field gradually diverges in the Y dimension.

The use of non-focusing material for the acoustic window 28 both improves the imaging characteristics of the transducer array 16 and simplifies manufacture of the acoustic window 28. In particular, the acoustic window 28 can be formed with a simple cylindrical shape, and in this way the need for compound curvatures in the region of the transducer is completely avoided, along with the need for precise registration between the transducer and the compound curvatures.

Figure 3:
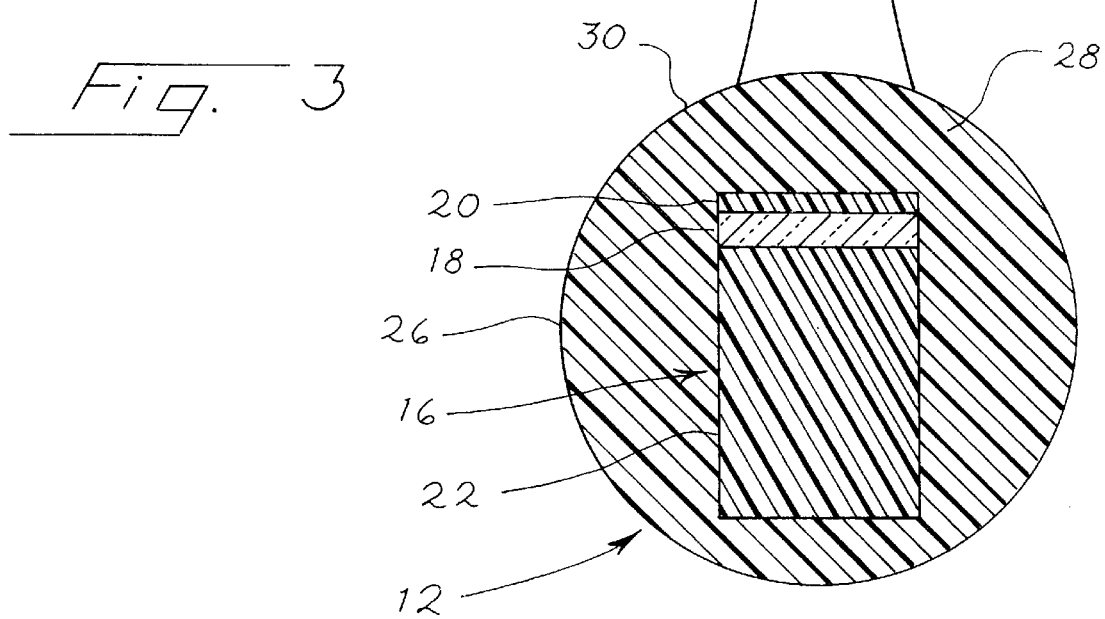
FIG. 3 is a partial sectional view showing the catheter of FIG. 1 at an intermediate stage of fabrication.

FIG. 3 illustrates one method of fabricating the end portion 26 of the transducer assembly 10. According to this method, a transducer array 16 as described above is connected to the distal end 14 of a conventional catheter 12. The transducer array 16 is placed within a cylindrical mold, which may for example be formed of anodized aluminum and provided with a nickel/Teflon coating, covered with a silicone-based mold release. A polymeric material such as urethane is molded to the catheter 12 around the array 16. Urethane in an uncured liquid state is poured into the mold, and the array 16 and catheter 12 are inserted deeply enough into the mold to ensure that the urethane will surround the array 16 and adhere to the distal end 14 of the catheter 12. After the urethane has cured, the assembly is removed from the mold. The mold release material ensures that the urethane will easily release from the mold after forming.

One potential drawback of the method of FIG. 3 is that it requires precise placement of the array within the mold, and such placement can complicate fabrication. An alternative method, which avoids such placement difficulties, uses a pre-formed end portion 26'. The end portion 26' is preferably molded from a thermoplastic material into the shape shown in FIG. 5. As shown in FIG. 5, the end portion 26' includes a longitudinally extending cavity 27'. The pre-formed end portion 26' has an outer shape in the desired final catheter geometry, and the inner cavity 27' is shaped to receive the array 16. Preferably, the inner cavity 27' conforms closely to the array 16 to eliminate pockets of air. This cavity 27' preferably has a flat surface adjacent the active surface of the array 16 and curved side surfaces that accommodate the electrical connections attached to the array 16. The cavity 27' is closed at the distal end, and the distal end of the end portion 26' is smoothly tapered to provide the desired end geometry for the catheter. The pre-formed end portion 26' may be created by injection molding or by using dies, glass tubing, a hot air source, and mandrels with the proper shapes for the desired outside dimensions and inner cavity.

Figure 6:
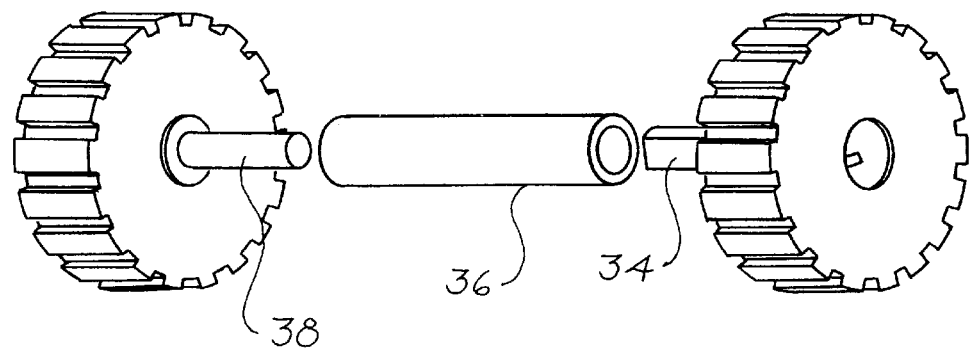
FIG. 6 is a schematic perspective view showing fixtures useful in assembling the embodiment of FIG. 4.
Figure 7:
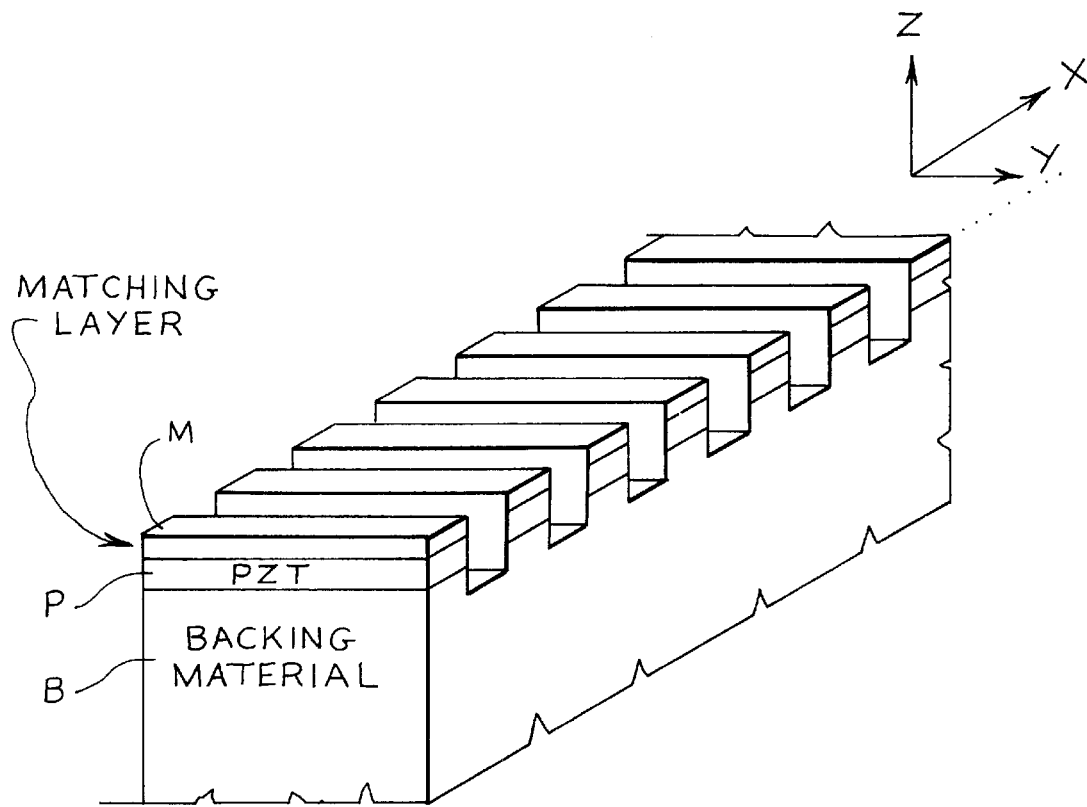
FIG. 7 is a schematic perspective view of a prior-art phased-array ultrasonic transducer.

As shown in FIG. 4, the pre-formed end portion 26' is pushed over the array 16. Assembly can be accomplished by inserting the assembly of the end portion 26' and the array 16 into a glass tube 36 having the proper inner diameter for the final assembly (FIG. 6). This tube can be for example approximately 1.5 inches in length. A die 38 having a concave recess shaped to correspond to the desired shape for the distal end of the end portion 26' is inserted into the glass tube 36. This die 38 is used to immobilize the end portion 26' and to apply pressure. A mandrel 34 is inserted into the opposite end of the glass tube 36 and is used to apply pressure opposing that of the die 38. Using a heating device such as a hot air knife, the assembly is then heated, and pressure is gently applied to the assembly by opposed forces on the mandrel 34 and the die 38. As the end portion 26' softens with heat, the pressure supplied by the die 38 and the mandrel 34 helps to eliminate any air gaps and to form and to bond the preformed end portion 26' to the array 16. The final assembly may then be cooled either by an air gun or otherwise, and the hardened, reflowed assembly may then be removed from the glass tubing 36. This method minimizes exposure of the array 16 to undesirably high temperatures.

In order better to define the presently preferred embodiments of this invention, the following details of construction are provided. It should be understood that these details are intended only by way of example.

The backing layer 22 may be formed as described in Sliwa U.S. Pat. No. 5,297,933, assigned to the assignee of this invention. The backing material disclosed in the Sliwa patent provides excellent acoustic properties while allowing the matching layer 20 and therefore the catheter 12 to be provided with an extremely low profile. The end portion 26, 26' may be formed of urethane (for example the resin CY8721 sold by Ciba-Geigy) or polyether block Amides (for example the resin Pebax sold by Autochem). Urethane may be used as an adhesive to secure the Pebax end portion to the catheter.

Preferably, flexible circuits as described in U.S. Pat. application Ser. No. 08/791,601, assigned to the assignee of the present invention, can be used in the catheter 12. If desired, the catheter 12 can be made disposable, and the interconnection system described in U.S. Pat. application Ser. No. 08/792,291, also assigned to the assignee of the present invention, can be used. The entire specifications of both of these U.S. patent applications are incorporated by reference herein.

From the foregoing, it should be apparent that an improved transducer assembly has been described that uses a non-focusing or defocusing material to form an acoustic window adjacent to the active surface of the transducer array. In this way the imaging characteristics of the catheter are improved, and manufacturing is simplified.

Of course, it should be understood that a wide range of changes and modifications can be made to the preferred embodiments described above. For example, the acoustic window may be formed of other materials having a speed of sound and acoustic impedance which match that of adjacent tissue. The diameter and length of the catheter and the end portion can all be adapted for the particular application, as can details of construction regarding the transducer array. If desired, the catheter can be provided with guidewire ports to allow the catheter to be inserted into the heart or blood vessels over a guidewire, or it can be provided with articulation wires to allow the catheter to be steered. Additionally, many other fabrication techniques can be used to fabricate the transducer assembly, and the broadest definitions of this invention are not intended to be limited to any particular fabrication technique.

It should therefore clearly be understood that the foregoing detailed description has discussed only a few of the many possible forms that the present invention can take. It is intended that only the following claims, including all equivalents, be regarded as a definition of this invention.

We claim:

1. A phased-array ultrasonic transducer comprising:
   a catheter comprising a distal end and defining a longitudinal axis;
   an array of transducer elements carried by the distal end of the catheter, said array defining an azimuthal axis oriented substantially parallel to the longitudinal axis;
   said catheter comprising an end portion positioned adjacent and radially outwardly from the array, said end portion conducting ultrasound waves to and from an active surface of the array with a speed greater than about 1250 m/sec and being substantially non-focusing to said ultrasound waves;
   said end portion characterized by a maximum cross-sectional dimension less than about 8 mm.

2. The invention of claim 1 wherein the maximum cross-sectional dimension is less than about 3.3 mm.

3. The invention of claim 1 wherein the maximum cross-sectional dimension is less than about 2 mm.

4. The invention of claim 1 wherein the end portion comprises an acoustic window positioned adjacent the active surface of the array, said window comprising a radially outer surface; wherein the radially outer surface is characterized by a radius of curvature substantially equal to one half of the maximum cross-sectional dimension of the end portion.

5. The invention of claim 4 wherein the end portion is substantially circular in cross section through the acoustic window.

6. The invention of claim 1 wherein the end portion comprises urethane.

7. The invention of claim 1 or 6 wherein the catheter comprises a catheter shaft, and wherein the end portion is molded to the catheter shaft around the array.

8. The invention of claim 7, wherein the end portion is molded as a single component.

9. The invention of claim 1 wherein the end portion comprises Pebax.

10. The invention of claim 1 or 9 wherein the end portion comprises a pre-molded element that is assembled over the array.

11. The invention of claim 10 wherein the end portion is adhered to the array by thermally softening the end portion.

12. The invention of claim 10, wherein the end portion is pre-molded as a single component.

13. The invention of claim 1 wherein said end portion conducts ultrasound waves to and from the active surface of the array with a speed greater than about 1410 m/sec.

14. The invention of claim 1 wherein said end portion conducts ultrasonic waves to and from the active surface of the array with a speed greater than or equal to about 1570 m/sec.

15. The invention of claim 1 wherein the end portion comprises a thermoformed thermoplastic material.

16. The invention of claim 1, wherein said end portion conducts ultrasound waves to and from an active surface of the array with a speed greater than about 1500 m/sec.

17. The invention of claim 1, wherein said end portion is substantially defocusing to said ultrasound waves.

18. The invention of claim 1, wherein said end portion conducts ultrasound waves to and from an active surface of the array with a speed matched to a speed of sound in tissue, wherein said tissue is blood.

19. The invention of claim 1 wherein said end portion conducts ultrasound waves to and from the active surface with a speed of 1570 m/sec +or −20%.

20. The invention of claim 1 wherein said end portion conducts ultrasound waves to and from the active surface with a speed of 1570 m/sec +or −10%.

21. The invention of claim 1 wherein said end portion conducts ultrasound waves to and from the active surface with a speed of 1570 m/sec +or −5%.

22. The invention of claim 1 wherein said end portion conducts ultrasound waves to and from the active surface with a speed of about 1570 m/sec.

23. The invention of claim 1 wherein the end portion comprises an acoustic window positioned adjacent the active surface of the array, said window comprising a radially outer surface shaped as a portion of a cylinder.

* * * * *

UNITED STATES PATENT AND TRADEMARK OFFICE
CERTIFICATE OF CORRECTION

PATENT NO. : 5,846,205
DATED : December 8, 1998
INVENTOR(S) : Michael G. Curley et al.

It is certified that error appears in the above-indentified patent and that said Letters Patent is hereby corrected as shown below:

In column 6, line 24, replace "5,297,933" with --5,297,553--.

Signed and Sealed this

Twenty-third Day of November, 1999

Attest:

Q. TODD DICKINSON

*Attesting Officer*     *Acting Commissioner of Patents and Trademarks*